US010342837B2

(12) United States Patent
Twilley et al.

(10) Patent No.: US 10,342,837 B2
(45) Date of Patent: Jul. 9, 2019

(54) EXTRACTS AND COMPOSITIONS OF HELICHRYSUM ODORATISSIMUM FOR PREVENTING AND TREATING SKIN CANCERS

(71) Applicant: University of Pretoria, Pretoria (ZA)

(72) Inventors: Danielle Twilley, Johannesburg (ZA); Namrita Lall, Silverlakes Golf Estate (ZA)

(73) Assignee: University of Pretoria, Pretoria (ZA)

( * ) Notice: Subject to any disclaimer, the term of this patent is extended or adjusted under 35 U.S.C. 154(b) by 441 days.

(21) Appl. No.: 15/027,038

(22) PCT Filed: Oct. 3, 2014

(86) PCT No.: PCT/IB2014/065038
§ 371 (c)(1),
(2) Date: Apr. 4, 2016

(87) PCT Pub. No.: WO2015/049666
PCT Pub. Date: Apr. 9, 2015

(65) Prior Publication Data
US 2016/0235797 A1 Aug. 18, 2016

(30) Foreign Application Priority Data
Oct. 3, 2013 (ZA) .................... 2013/07414

(51) Int. Cl.
| A61K 36/28 | (2006.01) |
| A61K 36/00 | (2006.01) |
| A61K 9/00 | (2006.01) |
| A61K 31/01 | (2006.01) |
| A61K 31/015 | (2006.01) |
| A61K 31/23 | (2006.01) |
| A61K 31/231 | (2006.01) |
| A61K 31/232 | (2006.01) |
| A61K 31/352 | (2006.01) |

(52) U.S. Cl.
CPC ............ *A61K 36/28* (2013.01); *A61K 9/0014* (2013.01); *A61K 31/01* (2013.01); *A61K 31/015* (2013.01); *A61K 31/23* (2013.01); *A61K 31/231* (2013.01); *A61K 31/232* (2013.01); *A61K 31/352* (2013.01); *A61K 2236/33* (2013.01)

(58) Field of Classification Search
None
See application file for complete search history.

(56) References Cited

U.S. PATENT DOCUMENTS

2011/0207806 A1  8/2011  Jia

OTHER PUBLICATIONS

Heyman H M et al. "Metabolomic comparison of selected *Helichrysum* species in search of anitviral properites", South African Journal of Botany SuidAfrifkanns, Tydskrift VirplantKunde, Foundation for Education, Science and Technology, Pretoria, SA, vol. 75, No. 2, Apr. 1, 2009 (Apr. 1, 2008), p. 404-405 (Year: 2009).*
International Search Report from International Application No. PCT/IB2014/065038, dated Jan. 12, 2014, 5 pages.
Facino, R.M. et al. "Anti-Erythematous and Photoprotective Activities in Guiea-Pigs and in Man of Topically Applied Flavonoids From Helichrysum-Italicum G. Don", Acta Therapeutica, vol. 14, No. 1, Jan. 1, 1988, pp. 323-346.
Fouche, G. et al. "In vitro anticancer screening of South African plants", Journal of Ethnopharmacology, vol. 119, No. 3, Oct. 1, 2008, pp. 455-461.
Heyman, H.M. et al. "Metabolomic comparison of selected *Helichrysum* species in search of antiviral properties", South African Journal of Botany—Suid-Afrikaans Tydskrift Virplantkunde, Foundation for Education, Science and Technology, Pretoria, SA, vol. 75, No. 2, Apr. 1, 2009, pp. 404-405.
Lall, N. et al. "In vitro inhibition of drug-resistant and drug-sensitive strains ofby enthnobotanically selected South African plants", Journal of Ethnopharmacology, Elsevier Ireland LTD, IE, vol. 66, No. 3, Oct. 9, 1999, pp. 347-354.
Legoale, P.B. et al. "Antiinflammatory and Antioxidant Flavonoids from Helichrysum kraussii and H. odoratissimum Flowers", Natural Product Communications, Natural Product Inc, US, vol. 8, No. 10, Jan. 1, 2013, pp. 1403-1404.
Puyvelde, L.V. et al. "Isolation of Flavonoids and a Chalcone From Helichrysum Odoratissimum and Synthesis of Helichrysetin", Journal of Natural Products, vol. 52, No. 3, May-Jun. 1989, pp. 629-633.
Mathekga, A.D.M. et al. "Antibacterial activity of South African *Helichrysum* species", South African Journal of Botany—Suid-Afrikaans Tydskrift Virplantkunde, Foundation for Education, Science and Technology, Pretoria, SA, vol. 34, No. 5, 1998, pp. 293-295.
Matic, I.Z. et al. "In vitro antitumor actions of extracts from endemic plant Helichrysum zivojinii", BMC Complementary and Alternative Medicine, vol. 13, No. 36, 2013, 12 pages.
Ramathal, D.C. et al. "Medicinal Plants Used by Rwandese Traditional Healers in Refugee Camps in Tanzania", Pharmaceutical Biology, Swets and Zeitlinger, vol. 39, No. 2, 2001, pp. 132-137.
Roman, B.I. et al. "Assessment of the Antineoplastic Potential of Chalcones in Animal Models", Current Medicinal Chemistry, vol. 20, No. 2, 2013, pp. 186-221.
Soliman, F.M. et al. "A new y-pyrone, sterols and triterpenes from Helichrysum bracteatum, Gazania nivea and Dimorphotheca ecklonis", Pharmacognosy Magazine, vol. 3, Issue 12, Oct.-Dec. 2007, pp. 213-217.
Ziaratnia, S.M. et al. "Isolation and identification of a Novel Chlorophenol from a Cell Suspension Culture of Helichrysum aureonitens", Chemical & Pharmaceutical Bulletin Nov. 2009, vol. 57, No. 11, Nov. 2009, pp. 1282-1283.

(Continued)

*Primary Examiner* — Michael Barker
*Assistant Examiner* — Randall Winston
(74) *Attorney, Agent, or Firm* — Meunier Carlin & Curfman LLC

(57) ABSTRACT

The present invention relates to extracts from *Helichrysum odoratissimum* for use in the prevention of and treatment of skin cancer. The invention also provides for pharmaceutical compositions containing the extract and to the use of medicaments containing the extract.

3 Claims, 2 Drawing Sheets

(56) References Cited

OTHER PUBLICATIONS

Berridge et al. "The biochemical and cellular basis of cell proliferation assays that use tetrazolium salts." Biochemica 4.1 (1996): 14-19.
Boik. "Natural compounds in cancer therapy." (2001).
Brunda et al. "Antitumor and antimetastatic activity of interleukin 12 against murine tumors." Journal of Experimental Medicine 178.4 (1993): 1223-1230.
Du Toit, et al. "Comparison of the antioxidant content of fruits, vegetables and teas measured as vitamin C aquivalents." Toxicology 166.1-2 (2001): 63-69.
Erkan et al. "Antioxidant activities of rosemary (Rosmarinus officinalis L.) extract, blackseed (Nigella sativa L.) essential oil, carnosic acid, rosmarinic acid and sesamol." Food Chemistry 110.1 (2008): 76-82.
Kuai et al. "Interleukin-8 associates with adhesion, migration, invasion and chemosensitivity of human gastric cancer cells" World journal of gastroenterology: WJG 18.9 (2012): 979.
Light et al. "Riding the wave: South Africa's contribution to ethnopharmacological research over the last 25 years." Journal of Ethnopharmacology 100.1-2 (2005): 127-130.
Lourens et al. "South African *Helichrysum* species: a review of the traditional uses, biological activity and phytochemistry." Journal of Ethnopharmacology 119.3 (2008): 630-652.
Mavundza et al. "Antioxidant activity and cytotoxicity effect of flavonoids isolated from Athrixia phylicoides." Journal of Medicinal Plants Research 4.23 (2010): 2584-2587.
McGaw et al. 2005. "Medicinal plants". In Ethics in agriculture—an African perspective, Edited by: van Niekerk, A. 67-83. Dordrecht, The Netherlands: Springer.
Street et al. "South African traditional medicinal plant trade—challenges in regulating quality, safety and efficacy." Journal of Ethnopharmacology 119.3 (2008): 705-710.
Stander et al. "In vitro effects of Sutherlandia frutescens water extracts on cell numbers, morphology, cell cycle progression and cell death in a tumorigenic and a non-tumorigenic epithelial breast cell line." Journal of ethnopharmacology 124.1 (2009): 45-60.
Tag et al. "Herbal medicines used in the treatment of diabetes mellitus in Arunachal Himalaya, northeast, India." Journal of Ethnopharmacology 141.3 (2012): 786-795.
Zheng et al. "Enhancement of the anti-herpetic effect of trichosanthin by acyclovir and interferon." FEBS letters 496.2-3 (2001): 139-142.

* cited by examiner

EXTRACTS AND COMPOSITIONS OF *HELICHRYSUM ODORATISSIMUM* FOR PREVENTING AND TREATING SKIN CANCERS

BACKGROUND OF THE INVENTION

The present invention relates to an ethanol extract from the leaves of the South African plant *Helichrysum odoratissimum*. The extract of the invention has been shown to have in vitro cytotoxic activity against A431 (epidermoid carcinoma) cells, as well as antioxidant activity.

Cytotoxicity of the extract was determined using the XTT (Sodium 3'-[1-(phenyl amino-carbonyl)-3,4-tetrazolium]-bis-[4-methoxy-6-nitro] benzene sulfonic acid hydrate) colorimetric assay. The XTT cell proliferation kit measures the reduction in viable cells in the presence of the plant extract. The extract showed strong cytotoxic activity against the A431 cells with a 50% inhibitory concentration ($IC_{50}$) of 15.5±0.15 µg/ml.

Antioxidant activity of the extract was determined using the DPPH (1,1-Diphenyl-2-picryl hydrazyl) assay. The extract exhibited a high radical scavenging activity with an $IC_{50}$ value of 5.13±0.07 µg/ml, which was observed in a dose-dependent manner.

According to the World Health Organization (WHO) 65-80% of the world's population in developing countries depends solely on plants for their primary health care needs. This is mainly due to the inaccessibility of poor income countries to access modern western medicines (Tag et al., 2012). In South Africa traditional herbal medicine is the primary source of healthcare for rural areas. It is estimated that approximately 27 million South Africans still rely on traditional medicine (Street et al., 2008). Traditional medicine is most prevalent in areas where Western health care is inaccessible or comparability higher in cost to traditional medicines. However the main reason for the high usage of traditional medicine is as a result of cultural beliefs (McGaw et al., 2005). Due to South Africa's large plant diversity it has been estimated that approximately 3000 plant species are used for their medicinal purposes (Light et al., 2005).

Cancer is one of the leading causes of death worldwide. In economically developed countries cancer is the leading cause of death whereas in developing countries it is the second leading cause. The prevalence of cancer is increasing in developing countries due to an increase in population and aging of the general population as well as adopting unhealthy lifestyles such as smoking, physical inactivity and unhealthy diets. Statistics based on GLOBOCAN 2008 estimate that approximately 12.7 million cancer cases and 7.6 million cancer deaths occurred in 2008 worldwide, of these cancer cases approximately 56% of cases and 64% of deaths occurred in the economically developing world (Dermal et al., 2011).

According to the World Health Organisation skin cancers, including non-melanoma and melanoma type cancers have increased over the past ten years. Worldwide there has been an estimate of 2-3 million non-melanoma skin cancer and 132,000 melanoma cases diagnosed in this period. The World Health Organisation further estimates that one in every three cancers diagnosed is a type of skin cancer.

*Helichrysum odoratissiumum* (L.) Sweet is from the Asteraceae family. It is a herbaceous shrub which is commonly known as Imphepho. This shrub is branched, has a strong aroma and is perennial which can grow to heights of 50 cm. The plant has silvery coloured leaves which are covered in fine hairs and yellow flowers which group at the tips of branches. *H. odoratissimum* has a wide geographical distribution in South Africa. It is also distributed in several other African countries including, Lesotho, Malawi, Mozambique, Swaziland and Zimbabwe.

*H. odoratissimum* has several medicinal traditional usages. The leaves and stems are burnt and the smoke inhaled which acts as a sedative or is used to treat insomnia. The roots are used to treat coughs and colds and an extract of the roots may be orally administered as a colonic cleanser. The ash of leafy twigs may be ingested and used to relieve coughs. Further, the ash obtained from the leaves may also be ingested to relieve vomiting. A tea from leaves is used to treat colic and stitch. Extracts or sap from the leaves and twigs of the plant may be used as eye drops to treat conjunctivitis. A decoction of the plant material is used to treat abdominal pains, female sterility, menstrual pain and/or eczema. An extract from the aerial parts of the plant is used to treat symptoms of dehydration. An infusion of leaves can also be used to treat symptoms associated with fever. In some cultures the plant is boiled and the extract obtained in this manner is used as an ointment for the treatment of pimples (Laurens at al., 2008).

SUMMARY OF THE INVENTION

According to a first aspect of the invention there is provided for a crude or purified extract from the plant *Helichrysum odoratissimum* for use in the prevention or treatment of skin cancer. The crude or purified extract of the invention may also be used in the treatment of other skin disorders and conditions. The other skin disorders and conditions preferably being selected from the group including eczema, scaly patched skin, redness, wound healing and/or the treatment of nodules.

The crude or purified extract exhibits strong antioxidant activity. Accordingly the antioxidant nature of the extract is useful for the treatment and prevention of skin conditions, particularly skin cancer. However, the crude or purified extract may also be used for the treatment and prevention of skin disorders and conditions selected from the group including eczema, scaly patched skin, redness, wound healing and the treatment of nodules.

The extract of the invention further provides a sun protection factor (SPF) boosting effect. Accordingly as a result of the SPF properties of the extract of the invention it may be used as a preventative treatment to combat the harmful effects of UV radiation.

The extract of the invention further exhibits strong cytotoxic activity towards cells associated with skin cancer. The extract also exhibits moderate to strong cytotoxic activity to non-cancerous cell lines, such as Chang liver cells, human embryonic kidney cells (Hek293) and mouse melanocyte cells (B16F10). With the respective $IC_{50}$ values of the extract being 57.43 µg/ml, 37.1±4.8 µg/ml and 25.43±0.55 µg/ml.

As used herein the term "skin cancer" refers to the group of cancers selected from basal cell carcinomas, squamous cell carcinomas, malignant melanoma and/or their precursors.

Preferably, the extract of the invention is an organic solvent-derived extract. The organic solvent used to prepare the extract may be selected from the group consisting of ethanol, methanol, butanol, chloroform, dichloromethane, acetone, and/or mixtures thereof. Preferably, the organic solvent is ethanol.

The extract of the invention may be derived from the roots, stem, bark, seeds, flowers, fruit, leaves and/or combinations of the aforementioned. However, preferably the extract is derived from the leaves of the plant.

According to a second aspect of the present invention there is provided for a pharmaceutical composition comprising a pharmaceutically effective amount of the crude or purified extract from the plant *Helichrysum odoratissimum* and a pharmaceutically acceptable carrier.

Preferably the pharmaceutical composition is topically administered to the subject. The pharmaceutical composition may be formulated in a preferred form topical selected from the group consisting of a skin lotion, cream, essence, toner, emulsion, soap, shampoo, rinse, cleanser, solution, ointment, jelly or suspension.

According to a third aspect of the invention there is provided for the use of a crude or purified extract of *Helichrysum odoratissimum* which exhibits cytotoxic activity towards cells exhibiting conditions associated with skin cancer in the preparation of a medicament for use in the prevention or treatment of skin cancer.

BRIEF DESCRIPTION OF THE FIGURES

Non-limiting embodiments of the invention will now be described by way of example only and with reference to the following figures.

DETAILED DESCRIPTION OF THE INVENTION

Figure 1:
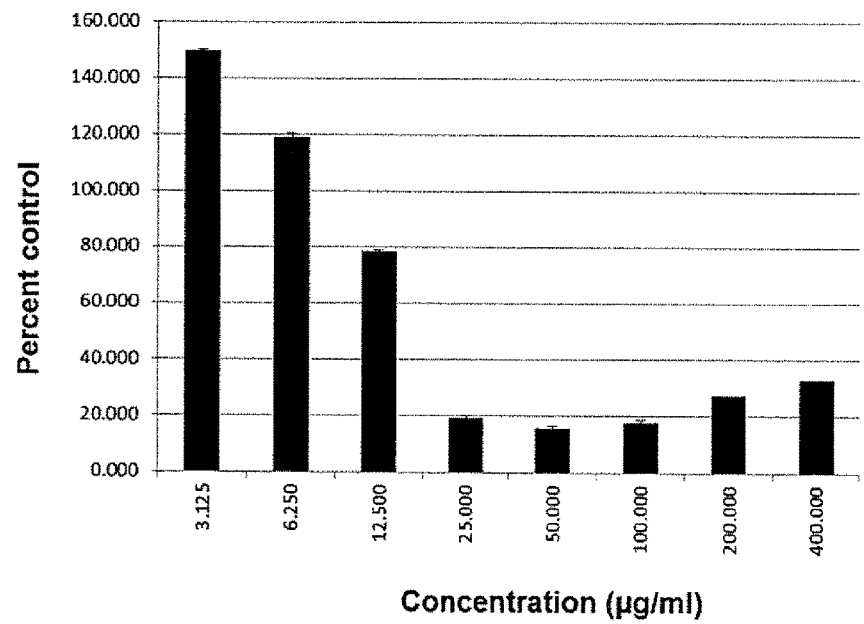
FIG. 1: Dose-dependent response of *Helichrysum odoratissimum* on A431 cells

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

In its broadest form, the present invention relates to crude or purified extracts from a *Helichrysum odoratissimum* plant. The extracts have both cytotoxic as well as antioxidant activity. The extracts are for use in the prevention and treatment of skin conditions in a subject, particularly the extracts are for use in the prevention and treatment of skin cancers.

It will be understood that prevention and treatment of a subject does not necessarily imply that symptoms of skin cancer are present. It will be further understood that the extract of the invention may be in the form of a crude extract, a purified extract or a pharmaceutical composition. The extract, pharmaceutical composition may be administered to a patient prior to a symptomatic state associated with skin cancers, or after a symptomatic onset of skin cancer in a subject.

Those skilled in the art will appreciate that there are a number of methods for synthesizing extracts from crude plant material. These methods include, among others, cutting, chopping, macerating and/or grinding raw plant material to at least one solvent in order to obtain a plant extract. It will also be appreciated that the crude plant material may be fresh material or dry plant material.

The solvent may be an organic solvent. Organic solvents typically used in the preparation of plant extracts include but are not limited to ethanol, methanol, butanol dichloromethane, chloroform, acetone and/or mixtures thereof.

As used herein the term "crude extract" refers to a concentrated preparation of a plant extract obtained by removing secondary metabolites from the crude plant material with the aid of a suitable solvent. This may be done, for example, by submerging the crude plant material in a suitable solvent, removing the solvent and consequently evaporating all or nearly all of the solvent. As used herein the term "purified extract" refers to an extract obtained by separating the constituent parts of the crude extract from each other. By way of a non-limiting example, the constituent parts of the crude extract may be separated from one another by separating the polar constituents from the non-polar constituents. In so doing the active polar and/or non-polar constituents may thus be concentrated.

As described herein the extract of the invention is an extract suitable for topical use on a subject. The subject may include a living animal, preferably a mammal and most preferably a human.

The extract can be prepared in any desired delivery form for example, as a spray, cream, lotion, balm, oil or solid, such as a roll-on, for personal use, or a solid strip. For instance, sprays can be prepared using conventional propellants, such as propane, butane, isobutane, either alone or in various mixtures known to those skilled in the art. Other conventional formulations, including known carriers and additives, will be readily apparent to those skilled in the art.

The extract may be formulated as a pharmaceutical composition by methods know to those skilled in the art. Pharmaceutically acceptable ingredients may be used. The term "pharmaceutically acceptable" refers to properties and/or substances which are acceptable for administration to a subject from a pharmacological or toxicological point of view. Further "pharmaceutically acceptable" refers to factors such as formulation, stability, patient acceptance and bioavailability which will be known to a manufacturing pharmaceutical chemist from a physical/chemical point of view.

The pharmaceutical composition of the invention containing the extract may be in a form suitable for topical use. Suitable forms of the pharmaceutical composition include, for example, lotions, creams, essences, toners, emulsions, soaps, shampoos, rinses, cleansers, solutions, ointments, jellies or suspensions.

The "suitable forms" of the pharmaceutical composition may be combined with "pharmaceutically acceptable carriers" and other elements known in the art to produce creams and lotions for use for general skin care. The pharmaceutical composition may further be combined with other ingredients which promote absorption by the skin.

By "pharmaceutically acceptable carrier" is meant a solid or liquid filler, diluent or encapsulating substance which may be safely used for the administration of the extract, pharmaceutical composition and/or medicament to a subject.

It will be appreciated that the crude or purified extract and/or pharmaceutical composition comprising the crude or purified extract may also be used in applications for animal and veterinary products.

The use of the extracts or medicaments containing the extract entails administration of an effective amount of the extract or a pharmaceutical composition containing the extract to a subject in order to prevent or treat a condition. The term "effective amount" in the context of preventing or treating a condition refers to the administration of an amount of the active plant extract to an individual in need of treatment, either a single dose or several doses of the extract or pharmaceutical composition containing the extract.

Although some indications have been given as to suitable dosages of the extract and/or pharmaceutical composition containing the extract, the exact dosage and frequency of administration of the effective amount will be dependent on several factors. These factors include the individual components used, the formulation of the extract or pharmaceutical composition containing the extract, the condition being treated, the severity of the condition, the age, weight, health and general physical condition of the subject being treated, and other medication that the subject may be taking, and other factors as are known to those skilled in the art. It is expected that the effective amount will fall within a relatively broad range that can be determined through routine trials.

The following examples are offered by way of illustration of the invention and not by way of limitation.

Example 1

Plant Collection and Extract Preparation

*H. odoratissimum* leaves were collected in KwaZulu-Natal, South Africa. The plant material was identified by qualified staff at the University of Pretoria and a voucher specimen (PRU 118963) was deposited in the Schweickerdt Herbarium (PRU), Pretoria, South Africa.

The air-dried aerial parts, comprising leaves and stems, of the plant were mechanically ground to produce a fine powder. The weighed samples were extracted with absolute ethanol for 48 hours and thereafter for 24 hours using fresh solvent. The solute was filtered with a Buchner funnel. Thereafter the filtered solute was evaporated to dryness using a vacuum rotary evaporator to give a dark green extract.

Example 2

In Vitro Cytotoxicity Assay

The A431 cell line was purchased from European Collection of Cell Cultures (ECACC). The cell culture medium, trypisn-EDTA, fetal bovine serum (FBS), phosphate buffer saline (PBS) and antibiotics were supplied by Highveld Biological (Pty) Ltd. (Modderfontein, Johannesburg, RSA). XTT Cell proliferation Kit II was obtained from Roche Applied Sciences, South Africa. The DPPH and Ascorbic acid were of analytical grade and supplied by Sigma Aldrich (St. Louis, Mo., USA).

The A431 cells were maintained in culture flasks containing Eagle's Minimum Essential Medium supplemented with 10% heat-inactivated FBS and 1% antibiotics (100 U/ml penicillin, 100 μg/ml streptomycin and 250 μg/ml fungizone). The cells were grown at 37° C. in a humidified incubator set at 5% $CO_2$. Cells were sub-cultured after they formed a monolayer on the flask. The cells were detached by treating them with trypsin-EDTA (0.25% trypsin containing 0.01% EDTA) for 10 minutes and then by adding complete medium to inhibit the reaction.

Cytotoxicity was measured by the XTT method using the Cell Proliferation Kit II. The method described by Zheng et al (2001) was used to perform the assay. The A431 cells were seeded (100 μl) in a 96-well microtitre plate (concentration $1 \times 10^5$ cells/ml). The plate was then incubated for 24 hours at 37° C. and 5% $CO_2$ to allow the cells to attach to the bottom of the wells. The *H. odoratissimum* extract was prepared to a stock solution of 20 mg/ml and added to the microtitre plate. Serial dilutions were made to range from a concentration of 400 μg/ml to 1,563 μg/ml. The microtitre plate was incubated for a further 72 hours. The control wells included vehicle treated cells exposed to 2% DMSO (sample concentration of 400 μg/ml) and a medium only control. After the 72 hour incubation period the XTT reagent (50 μl) was added to a final concentration of 0.3 mg/ml and the plate was then further incubated for a further 2 hours. After the incubation the absorbance of the colour complex was read at 490 nm with a reference wavelength set at 690 nm using a BIO-TEK Power-Wave XS multi-well plate reader. The assay was performed in triplicate to calculate an $IC_{50}$ of the cell population for each extract. Results were analysed using the GraphPad Prism 4 program.

The *H. odoratissimum* plant extract was evaluated for its anti-cancer activity on A431 cells using the XTT colorimetric assay. The assay is based on the ability of viable cells to reduce the yellow tetrazolium salt to an orange formazan product (Berridge et al., 1996). The ethanolic extract of *H. odoratissimum* showed promising cytotoxicity against A431 cells with an $IC_{50}$ value of 15.5±0.15 μg/ml (FIG. 1). According to the US National Cancer Institute an extract is considered to have in vitro cytotoxic activity if the $IC_{50}$ is less than 20 μg/ml after a 72 hour incubation period (Boik, 2001).

The XTT assay on the A431 cell lines clearly showed that the ethanolic extract of the invention has cytotoxic activity.

Example 3

Anti-Oxidant Activity-DPPH Assay

The method of du Toit et al (2001) was followed to determine the radical scavenging capacity (RSC) of the *H. odoratissimum* extract. Slight modifications to the method were made and are described briefly. Stock solutions of Vitamin C and the extract were prepared at concentrations of 2 mg/ml and 10 mg/ml respectively. To each well in the top row of a 96-well plate, 200 μl of distilled water was added. To the rest of the wells 110 μl of distilled water was added as a medium. Twenty microliters of extract was added to the first top wells, in triplicate, followed by serial dilution with final concentrations ranging from 3.9 μg/ml to 500 μg/ml for the extracts and 0.781 μg/ml to 100 μg/ml for Vitamin C (2010). Finally 90 μl of 0.04M DPPH ethanolic solution was added to each well, except for the negative control where distilled water was added instead. The plates were left in a dark room to develop for 30 minutes. The RSC of the extract was determined using a BIO-TEK Power-Wave XS multi-plate reader at a wavelength of 515 nm, using KC junior software. The $IC_{50}$ value of the extract was calculated using GraphPad Prism 4 software. Finally, the Vitamin C equivalent of the extract was calculated as follows:

($IC_{50}$ of extract×200 mg Vitamin C)/$IC_{50}$ of Vitamin C.

Figure 2:
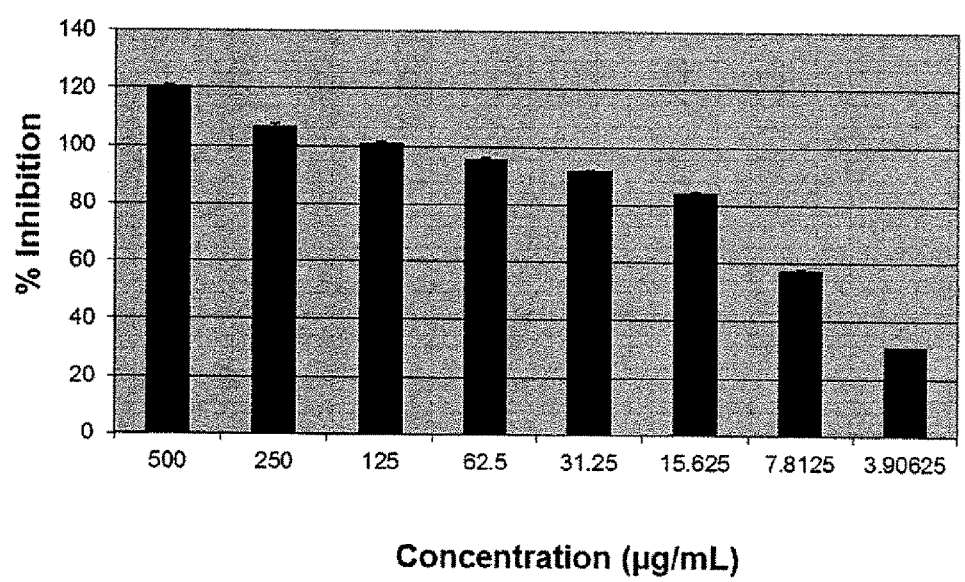
FIG. 2: Antioxidant activity of *H. odoratissimum* extract using the DPPH assay.

The DPPH assay preformed on the *H. odoratissimum* extract was used to evaluate the radical scavenging activity of the extract. The assay is based on the reduction of a purple free radical to a yellow stable compound in the presence of an antioxidant. The amount of reduction is a measurement of the effectivity of the antioxidant, in other words it depends on the hydrogen donating ability of the antioxidant (Erkan et al., 2008). The extract showed a dose-dependent response with a strong antioxidant activity with an $IC_{50}$ value of 5.13±0.07 µg/ml (FIG. 2).

The DPPH assay clearly showed that the ethanolic extract of the invention has strong antioxidant activity.

Example 4

SPF Activity

Due to the strong antioxidant activity exhibited by the extract a SPF clinical trial was conducted to determine whether the extract showed SPF boosting properties. The extract was tested according to the procedures as described in the SANS 1557:2013 South African National Standard—Sunscreen products and the international standards—ISO (First edition 2010 Nov. 15)—Cosmetics—Sun protection test methods—In vivo determination of the sun protection factor (SPF).

The objective was to evaluate the static (dry) in vivo Sun Protection Factor (SPF) of the extract by conducting an in vivo test on a minimum of ten healthy human volunteers.

In this test the extract was added to the Sunscreen Standard SPF 15 (P3) to determine whether the extract could boost the SPF of the reference standard. The results achieved for the extract indicates a mean SPF of 32.4 which indicates that the extract boosted the SPF of the reference standard due to the high antioxidant content which in turn was able to reduce UV-induced erythema.

Example 5

Cytokine Production

The levels of cytokine production (IL-8 and IL-12) from cell supernatants were measured by enzyme-linked immunosorbent assay (ELISA) according to the manufacturer's protocol (BD Biosciences, San Diego, Calif., USA). The levels of IL-12 were determined as it was reported to act as a potential anti-tumour agent (Brunda et al. 1993). IL-8 was measured as it plays a major role in the progression of various cancer cells by invasion, migration, adhesion, proliferation (Kuai et al. 2012). Briefly U937 cells were plated at a concentration of $2.5×10^5$ cell per well in a 24-well plate. The cells were incubated for 24 h with 0.1 µg/ml PMA at 37° C. and 5% $CO_2$ to allow the monocytes to differentiate into macrophages. The cells were treated with various concentrations of *H. odoratissimum* extracts. Controls included 20 µg/ml pentoxifylline, 5 µg/ml phytohemagglutinin (PHA), as well as vehicle-treated control cells (1% DMSO) and a medium only control. The cells were incubated for a further 20 hrs and thereafter centrifuged at 980 rpm for 5 min to collect the cell free supernatant and analyse the concentration of IL-8 and IL-12.

The cytotoxicity of the *H. odoratissimum* extract was first analyzed on the U937 cells to determine $IC_{50}$ values at which the extract could be tested when evaluating the cytokine profile and to ensure that the concentrations of phytohemagglutinin (PHA) and pentoxifylline, used to determine the cytokine profile, was not toxic to the U937 cells. The cytotoxicity of the extract and the relevant controls are shown in Table 1.

TABLE 1

Cytotoxicity of *H. odoratissimum*, PHA and pentoxifylline on U937 cells

| Sample | $IC_{50}$ (in µg/ml) |
|---|---|
| *H. odoratissimum* | 20.3 ± 3.1 |
| PHA | 318 ± 7.8 |
| Pentoxifylline | 170 ± 6.4 |

*H. odoratissimum* was analyzed at 20 µg/ml, 15 µg/ml, 10 µg/ml and 5 µg/ml to determine whether the extract was able to induce the production of IL-12 and inhibit the production of IL-8 in phytohemagglutinin (PHA) stimulated U937 cells, the results of which are depicted in Table 2.

TABLE 2

Production of IL-12 and IL-8 in U937 cells and cell viability

| Samples | IL-12 (pg/ml) | IL-8 (pg/ml) | Cell viability in % |
|---|---|---|---|
| *H. odoratissimum* at 20 µg/ml | 4.09 ± 2.2 | 70.1 ± 0.12 | 74% ± 1.6 |
| *H. odoratissimum* at 15 µg/ml | 5.65 ± 2.8 | 73.8 ± 1.9 | 101% ± 1.9 |
| *H. odoratissimum* at 10 µg/ml | 7.55 ± 3.7 | 95.3 ± 1.9 | 105% ± 6.3 |
| *H. odoratissimum* at 5 µg/ml | 12.4 ± 7.0 | 103 ± 6.1 | 128% ± 1.6 |
| PHA at 5 µg/ml | 9.49 ± 3.8 | 107 ± 5.6 | 101% ± 0.3 |
| DMSO at 1% | 4.60 ± 1.4 | 44.8 ± 4.9 | 100% |
| Pentoxifylline at 20 µg/ml | 1.37 ± 0.9 | 51.2 ± 7.2 | 106% ± 2.2 |
| Medium and cells | 4.71 ± 0.5 | 123 ± 6.0 | 117% ± 0.3 |

*H. odoratissimum* was able to enhance the production of IL-12 when compared to the production of IL-12 in the medium control at 5 µg/ml, 10 µg/ml and 15 µg/ml however, as the concentration of the extract increased the production of IL-12 decreased, which could be due to the lowered viability of the cells. The DMSO control showed similar production of IL-12 when compared to the medium control, whereas the PHA control showed an increase in IL-12 and pentoxifylline showed an inhibition.

A similar pattern was noted with the production of IL-8 as with the production of IL-12, with a high concentration of *H. odoratissimum* correlating with a lower production of IL-8. At all the concentrations of the extract the IL-8 was inhibited when compared to that of the medium control. DMSO seemed to show the highest inhibition of IL-8, which could also explain the inhibition seen at the extract, as DMSO was used to prepare the stock concentrations of the extract.

Example 6

Light Microscopy Showing Apoptosis

Haematoxylin and eosin staining was used to analysis the morphological characteristics of the A431 cells after exposure to 15 µg/ml ($IC_{50}$), 30 µg/ml ($2IC_{50}$) and 7.5 µg/ml (½$IC_{50}$) of *H. odoratissimum* and to determine what mechanism of cell death was taking place. The specific concentrations of extract were chosen due to the anti-proliferative activity that was observed. Exponentially growing cells were seeded at 100,000 cell per well in 6-well plates on heat-sterilized coverslips. After 24 h incubation at 37° C. and 5% humidity for cell adherence, cells were exposed to 15 µg/ml, 30 µg/ml and 7.5 µg/ml of *H. odoratissimum* extract including vehicle-treated control cells (2% DMSO); cells propagate in growth medium, as well as 0.025 µg/ml Actinomycin D and incubated for 72 h at 37° C. Cells were then fixed in Bouin's fixative for 30 min and stained by standard haematoxylin and eosin staining procedures (Stander et al. 2009).

Figure 3:
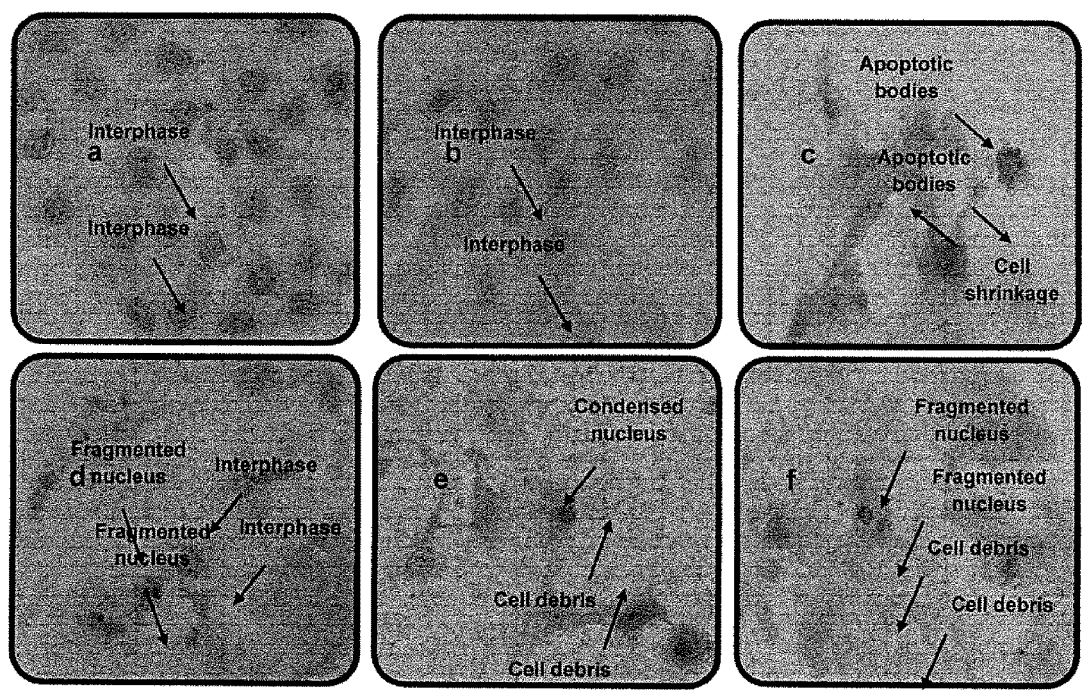
FIG. 3: Haematoxylin and eosin staining of A431 cells (a) medium-only control (b) vehicle-treated control (c) 15 μg/ml *H. odoratissimum* (d) 7.5 μg/ml *H. odoratissimum* (e) 30 μg/ml *H. odoratissimum* and (f) Actinomycin ID at 20× magnification, after 72 h of exposure

*H. odoratissimum* was qualitatively analysed at 15 µg/ml ($IC_{50}$), 30 µg/ml ($2IC_{50}$) and 7.5 µg/ml ($½IC_{50}$) to determine the influence on A431 cell morphology after 72 hrs exposure. The influence of *H. odoratissimum* was compared to a medium control, vehicle-treated control and Actinomycin D (FIG. 3).

Control cells propagated in growth medium (FIG. 3*a*) and vehicle-treated controls (FIG. 3*b*) showed normal signs of cell division and the presence of interphase cells. *H. odoratissimum* treated cells showed an increase in morphological characteristics associated with apoptosis. Cells exposed to 15 µg/ml and 30 µg/ml of extract showed no normal cell proliferation and signs of cell death started to appear. Typical characteristics of apoptosis were viewed such as apoptotic body formation and cell shrinkage at 15 µg/ml (FIG. 3*c*) as well as condensed nucleus and cell debris with a low cell viability at 30 µg/ml (FIG. 3*e*). Cells exposed to 7.5 µg/ml showed signs of cell death such as fragmented nucleus with normal signs of cell death also noticeable (FIG. 3*d*). In cells exposed to Actinomycin D, a great amount of cell death and total loss of cell viability was observed with signs of compacted and fragmented nucleus (FIG. 3*f*).

Example 7

Pure Compounds and Essential Oils

Approximately 130 g of the prepared methanolic *Helichrysum odoratissimum* extract was subject to silica gel column chromatography with hexane fraction (Hex):ethyl acetate (EtOAc) mixtures of increasing polarity (100:0 to 0:100) followed by ethyl acetate (EtOAc):methanol (MeOH) mixtures with increasing polarity (100:0 to 0:100). In total 220 fractions were collected and similar fractions were combined according to thin-layer chromatographic (TLC) profile to obtain 18 major fractions. Fraction B was subject to another silica gel column chromatography with hexane fraction:dichloromethane mixtures of increasing polarity (100:0 to 0:100), which yielded compound 1. Fraction C and E yielded essential oil numbers 2 and 1 respectively. Fraction F yielded compound 2 and fractions P and Q yielded the last two compounds.

These compounds and essential oils have been isolated from the methanolic leaf and stem extract from *Helichrysum odoratissimum*.

a. Essential oil 1 composed of:
  i. Eucalyptol
  ii. Caryophyllene
  iii. 1,4,7-Cycloundecatriene, 1,5,9,9-tetramethyl-, Z,Z,Z-
  iv. Hexadecanoic acid, methyl ester
  v. 9,15-Octadecadienoic acid, methyl ester, (Z,Z)-
  vi. 9,12,15-Octadecatrienoic acid, ethyl ester, (Z,Z,Z)-
b. Essential oil 2 composed of:
  i. Copaene
  ii. 1H-Cycloprop[e]azulene, decahydro-1,1,7-trimethyl-4-methylene-, [1aR-(1a.alpha.,4a.beta.,7.alpha.,7a.beta.,7b.alpha.)]-
  iii. 1H-Cycloprop[e]azulene, decahydro-1,1,7-trimethyl-4-methylene-, [1aR-(1a.alpha.,4a.beta.,7.alpha.,7a.beta.,7b.alpha.)]-
  iv. Naphthalene, decahydro-4a-methyl-1-methylene-7-(1-methylethenyl)-, [4aR-(4a.alpha.,7.alpha.,8a.beta.)]-
c. Compound 1—5,21-dimethylpentacosane
d. Compound 2—Tetracosane
e. Third and fourth compound are still being analysed for identification

REFERENCES

Berridge, M. V. et al. 1996 Biochemica 4, 14-19.
Balk, J. 2001. Natural Compounds in Cancer Therapy. Oregon Medical Press, Minnesota, USA.
Brunda M. J. et al. 1993 J. Exp Med 178: 1223-1230.
Du Toit, R. et al. 2001 Toxicology 166, 63-69.
Erkan, A. et al. 2008 Food chemistry 110: 76-82.
Jermal, A. et al. 2011 CA Cancer Journal for Clinicians 61, 69-90.
Kuai W X, et al. 2012 World J Gastroenterol 18(9): 979-985.
Light, M. E. et al. 2005 Journal of Ethnopharmacology (100), 127-130.
Laurens, A. C. U. et al. 2008 Journal of Ethnopharmacology, 119(3), 630-652.
Mavundza. et al. 2010 Journal of Medicinal Plant Research 23, 2584-2587.
McGaw, L. et al. 2005. Medicinal plants. In: van Niekerk, A. (Ed.), Ethics in Agriculture—An African Perspective. Springer, Dordrecht, The Netherlands, pp. 67-83.
Street, R. A. et al. 2008 Journal of Ethnopharmacology (199), 705-710.
Stander A. et al. 2009 J Ethnopharmacol 124: 45-60.
Tag, H. et al. 2012 Journal of Ethnopharmacology 141, 786-795.
Zheng, Y. T. et al. 2001 FEBS Letters 496, 139-142.

The invention claimed is:

1. A method of treating skin cancer, the method comprising administering to a subject an effective amount of a crude or purified extract of *Helichrysum odoratissimum*, wherein the extract exhibits cytotoxic activity towards cells exhibiting conditions associated with skin cancer.

2. The method according to claim 1, wherein the skin cancer is selected from the group consisting of basal cell carcinoma, squamous cell carcinoma, malignant melanoma, and combinations thereof.

3. The method of claim 1, wherein the crude or purified extract is administered in an amount of from 3.125 µg/ml to 400 µg/ml.

* * * * *